United States Patent [19]

Kusakabe et al.

[11] 4,224,407
[45] Sep. 23, 1980

[54] ASSAY OF L-LYSINE

[75] Inventors: Hitoshi Kusakabe, Kyoto; Akira Kuninaka, Choshi; Kenji Soda, Uji, all of Japan

[73] Assignee: Yamasa Shoyu Kabushiki Kaisha, Choshi, Japan

[21] Appl. No.: 15,177

[22] Filed: Feb. 26, 1979

[30] Foreign Application Priority Data

Sep. 22, 1978 [JP] Japan .................... 53-115867

[51] Int. Cl.$^2$ ............................................. C07G 7/02
[52] U.S. Cl. ..................................... 435/25; 435/191; 435/945
[58] Field of Search .......................... 435/25–28, 435/115, 189, 191, 945

[56] References Cited

U.S. PATENT DOCUMENTS 3,235,337  2/1966  Artis .................... 435/191 X
3,852,157  12/1974  Rubenstein et al. ......... 435/25 X

OTHER PUBLICATIONS

Greenberg, *Metabolic Pathways*, Third Edition, vol. 3, pp. 38–47 (Academic Press, 1969).
Glick, *Methods of Biochemical Analysis*, vol. IV, pp. 285–306 (Interscience Publishers, 1957).
*Analytical Chemistry*, vol. 49, pp. 225–231 (Academic Press, 1972).
*Analytical Chemistry*, vol. 89, pp. 283–289 (Academic Press, 1978).
Guilbault, *Handbook of Enzymatic Methods of Analysis*, pp. 217–219 (Marcel Dekker, Inc., 1976).

*Primary Examiner*—Thomas G. Wyse
*Attorney, Agent, or Firm*—Wenderoth, Lind & Ponack

[57] ABSTRACT

L-lysine contained in a sample can be efficiently determined by using the L-lysine α-oxidase. The preferred enzyme is an L-lysine α-oxidase, that is, a novel L-amino acid oxidase having very high substrate-specificity to L-lysine is produced by culturing a specific microorganism belonging to Trichoderma in a medium.

5 Claims, 6 Drawing Figures

ASSAY OF L-LYSINE

BACKGROUND OF THE INVENTION

1. Field of the Invention

This invention relates to the use of an L-lysine α-oxidase having very high substrate-specificity with respect to L-lysine, that is, an L-lysine α-oxidase, and more particularly to the utilization of the L-lysine α-oxidase for determination of L-lysine.

2. Description of the Prior Art

L-lysine is one of the essential amino acids. The L-lysine, however, is generally contained in a lower amount in vegetable proteins and, for example, is considered as the limiting amino acid in rice, rye and corn, and as the primary limiting amino acid in wheat, sesame, oats, etc. The enrichment of L-lysine in vegetable foods and feeds has been acknowledged to be effective in improving their nutritive values and has been carried out in the world. Thus, the assay of L-lysine contained in natural foods and enriched foods is very important in view of the science of nutrition. The assay of L-lysine is also important in the nutritive conditioning of human beings and domestic animals as well as in the diagnosis of metabolic disorders. The production and demand of L-lysine have been increased in the field of food and feed industries. On the other hand, the relations between the L-lysine level in vivo and the nutritive and pathologic conditions in vivo have been clarified in the field of nutritive physiology and pathologic biochemistry. Thus, there has been a need for the establishment of a simple and sensitive method of determining L-lysine.

Examples of methods for determination of L-lysine which have hitherto been developed are chromatographic methods such as paper chromatography, thin-layer chromatography, ion-exchange chromatography, and gas-liquid chomatography specific chemical methods, microbial methods, and enzymic methods. The conventional enzymic methods include (1) determination of carbon dioxide generated from L-lysine contained in a sample by the action of L-lysine decarboxylase (cf. Methods of Biochemical Analysis, Vol. IV, pp. 285–306, 1957, Interscience Pushlishers Inc.) (2) determination of the amount of oxidized NADH when an L-lysine-containing sample is incubated with α-ketoglutaric acid and saccharopin dehydrogenase (cf. Analytical Biochemistry, Vol. 49, p.p. 225–231, 1972), and (3) determination of $\Delta^1$-piperideine-6-carboxylic acid which is formed by incubating L-lysine and α-ketoglutaric acid in the presence of L-lysine: α-ketoglutaric acid ε-aminotransferase (cf. Analytical Biochemistry, Vol. 87, p.p. 283–289, 1978).

Hitherto there have been reports on the presence of L-amino acid oxidases in microorganisms, snake venom, the rat kidney, the fowl liver, and invertebrates (Arch Biochem. Biophys. Vol 146, p.p. 54–63, 1971; Journal of Bacteriology, Vol 121, No. 2, p.p. 656–662, Feb., 1975; and the Tanpakushitsu.Kakusan Koso, Vol. 17, No. 1, pp. 42–55, 1972). An L-amino acid oxidase having very high substrate-specificity to L-lysine has never been known in the art. In other words, known L-amino acid oxidases exhibit only very low enzyme activities to L-lysine except that an L-amino acid oxidase preparation derived from the turkey liver exhibits a high activity to L-lysine. However, the turkey liver enzyme also effectively oxidizes several amino acids other than L-lysine, such as L-arginine, L-hietidine and L-ornithine, at the rate equivalent to or greater than the rate of oxidizing L-lysine. Thus, the oxidase preparation can not be considered to be an enzyme having especially high substrate-specificity to L-lysine.

SUMMARY OF THE INVENTION

It is an object of this invention to provide a use of L-lysine α-oxidase, that is, an L-amino acid oxidase which has the capability of forming α-keto-ε-aminocaproic acid, ammonia and hydrogen peroxide via the oxidative deamination of L-lysine in the presence of water and oxygen with a very low Km value with respect to L-lysine and the high substrate-specificity to L-lysine.

A specific object of this invention is to provide an assay method for L-lysine which comprises oxidizing L-lysine contained in a sample with L-lysine α-oxidase in the presence of oxygen and then determining the quantity of consumed oxygen in the reaction mixture or the quantity of produced hydrogen peroxide, ammonia, α-keto-ε-aminocaproic acid or $\Delta^1$-piperideine-2-carboxylic acid.

DESCRIPTION OF THE INVENTION

Figure 1:
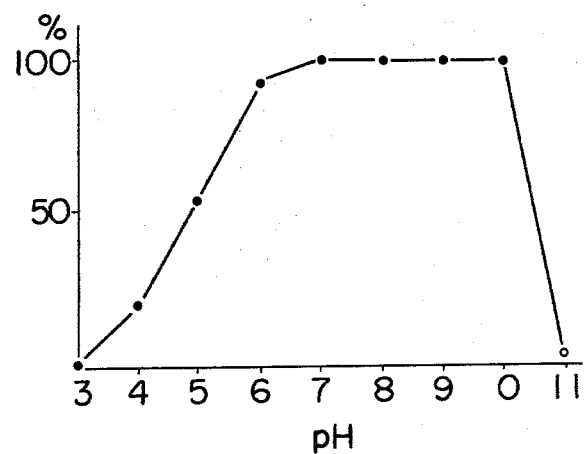
FIG. 1 is a graph of a curve indicating the pH stability of L-lysine α-oxidase.

In accordance with the present invention, the specific determination of L-lysine can be performed sensitively and simply as compared with the above-described conventional methods by incubating the present enzyme with a sample containing L-lysine in the presence of water and oxygen to deaminate L-lysine oxidatively; and determining the quantity of oxygen consumed in the course of the enzyme reaction, or the amount of hydrogen peroxide, ammonia, α-keto-ε-aminocaproic acid or $\Delta^1$-piperideine-2-carboxylic acid, which is an intramolecular dehydrated form of α-keto-ε-aminocaproic acid, produced in the course of the enzymatic reaction.

By the term "L-lysine α-oxidase" employed in the present invention, is meant an enzyme which acts specifically on L-lysine, has very strong affinity for L-lysine, and catalyzes the oxidative deamination of L-lysine to produce α-keto-ε-aminocaproic acid, ammonia, and hydrogen peroxide as shown in the following reaction formula.

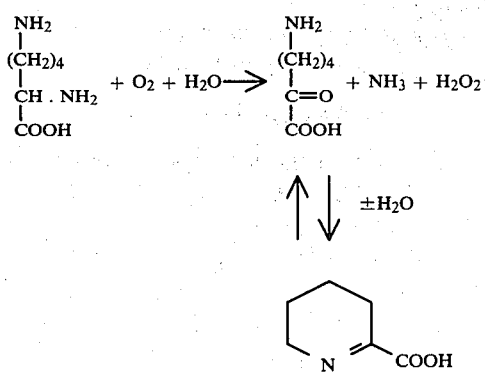

The method of the present invention is characterized by the utilization of the enzymic action of L-lysine α-oxidase which acts specifically on L-lysine, and should not be restricted by the origin and derivation of the enzyme. The L-lysine α-oxidase suitable for the practice of the present invention is exemplified by the enzyme which was produced by molds belonging to the genus Trichoderma. The mold belonging to the genus Trichoderma having the ability to produce L-lysine α-oxidase is represented by the new strain, *Trichoderma viride* Y244-2 90 under FERM-P No. 4246 and ATCC No. 20536 which was isolated from the soil collected at Mt. Mitsumine, Saitama, Japan.

I. Physical and Chemical Properties of L-lysine α-oxidase

The L-lysine α-oxidase of the present invention has a catalytic action and a substrate-specificity as described above. Its physical and chemical properties of the purified enzyme preparation which was produced and isolated according to the process for preparation thereof described in Example 1 are as follows.

(1) Enzymic Action

The enzyme of the present invention deaminates oxidatively the α-amino groups of an L-amino acid in the presence of oxygen and produces an α-keto acid, ammonia and hydrogen peroxide, in the same manner as in the conventional L-amino acid oxidases but is a novel L-amino acid oxidase characterized by its very high substrate-specificity. When L-lysine is used as a substrate, one mol of L-lysine requires one mol each of oxygen and water to produce one mol of α-keto-ε-aminocaproic acid and one mol each of ammonia and hydrogen peroxide as shown in the following reaction formula.

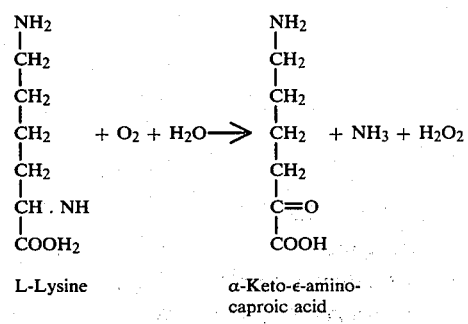

L-Lysine      α-Keto-ε-amino-
              caproic acid

(2) Substrate Specificity

A variety of substrates listed in the following table were subjected to the action of the purified enzyme of the present invention, and the relative enzyme activities thereof were determined according to the oxygen-electrode method. As a result, the present enzyme showed a high substrate-specificity to L-lysine. In this connection, the enzyme of the present invention also showed some activities to L-ornithine, L-phenylalanine, L-histidine, and L-arginine. The affinity of the enzyme for each of these amino acids was much lower than that for L-lysine: the Km value of the enzyme for L-lysine was very low ($4 \times 10^{-5}$ M), whereas the values for L-ornithine and L-phenylalanine were $4.4 \times 10^{-4}$ M and $1.4 \times 10^{-2}$ M, respectively. The Km values for the other amino acids were considered to be as much as $1 \times 10^{-2}$ to $2 \times 10^{-2}$ M. Therefore, the enzyme of the present invention was found to be an L-amino acid oxidase which exhibits almost no action on the amino acids other than L-lysine when the concentration of the substrate was low, and to have a very high substrate-specificity to L-lysine. Thus, the present enzyme is referred to as L-lysine α-oxidase [E C 1, 4, 3; L-lysine: oxygen oxidoreductase (deaminating)].

| Substrate (10 mM) | Relative activity (%) | Substrate (10 mM) | Relative activity (%) |
|---|---|---|---|
| L-Lysine | 100.0 | L-Serine | <0.5 |
| L-Ornithine | 18.2 | L-Threonine | <0.5 |
| L-Phenylalanine | 8.3 | D-Lysine | <0.5 |
| L-Arginine | 6.1 | ε-Aminocaproic acid | <0.5 |
| L-Histidine | 3.8 | δ-Aminovareric acid | <0.5 |
| L-Asparagine | <0.5 | Putrescine | <0.5 |
| L-Glutamine | <0.5 | Cadaverine | <0.5 |
| L-Tryptophan | <0.5 | L-Citrulline | <0.5 |
| L-Methionine | <0.5 | Homocitrulline | <0.5 |
| L-Proline | <0.5 | 2,4-Diaminobutyric acid | <0.5 |
| L-Glutamic acid | <0.5 | α,β-Diaminopropionic acid | <0.5 |
| L-Aspartic acid | <0.5 | ε-N-Acetyl-L-lysine | <0.5 |
| L-Cysteine | <0.5 | D,L-Homolysine | 31.1 |
| L-Glycine | <0.5 | δHydroxy-lysine | 37.1 |
| L-Alanine | <0.5 | L-Lysine hydroxamate | 62.1 |
| L-Hydroxyproline | <0.5 | L-Lysine ethyl ester | 83.3 |
| L-Leucine | <0.5 | S-(β-Aminoethyl)-L-cysteine | 9.8 |
| L-Isoleucine | <0.5 | S-(β-Aminopropyl)-L-cysteine | 34.8 |
| L-Valine | <0.5 | S-(β-4-Pyridylethyl)-L-cysteine | 2.7 |

(3) Measurement of the Enzyme Activity

The activity of the present enzyme was measured in accordance with Soda's method (Analytical Biochemistry Vol. 25, p. 228, 1968) in the following manner. A reaction mixture consisting of 0.7 ml of 0.1 M potassium phosphate buffer (pH 8.0), 0.1 ml of catalase (750 U/ml), 0.1 ml of 0.1 M L-lysine solution and 0.1 ml of the present enzyme solution was incubated at 37° C. for 20 minutes with gentle shaking. After the incubation the reaction was terminated by the addition of 0.1 ml of 25% trichloroacetic acid. To the resulting reaction mixture were added 1.9 ml of 1 M acetate buffer (pH 5.0) and 0.8 ml of 0.1% 3-methyl-2-benzothiazolone hydrazone hydrochloride solution. The mixture was further incubated at 30° C. for 30 minutes and then allowed to cool to room temperature, after which measurement of optical density at 318 nm was carried out. The formed α-keto-ε-aminocaproic acid thus formed was determined from the resulting calibration curve. One unit of the enzyme was defined as the quantity of the enzyme catalyzing the formation of 1 μmol of α-keto-ε-aminocaproic acid at 37° C. per minute. The relative activity of the enzyme was also assayed by manometric and polarographic determination of the oxygen consumption.

(4) Optimum pH

The enzyme activity for L-lysine at various pH values was determined by using acetate buffers (pH5, pH6), phosphate buffers (pH6, pH7 and pH8), Tris-hydrochloric acid buffers (pH 7.5, pH 8.0, pH 8.5 and pH 9.0), and glycine-sodium hydroxide buffers (pH 9.0, pH 9.5 and pH 10.0). As a result, the optimum pH was found to be in the vicinity of 8 to 9.

(5) pH Stability and Thermal Stability

After the enzyme was incubated at 45° C. for 20 minutes in the range of pH 3 to 11, and then the remaining enzyme activity was determined. The enzyme was found to be stable at the pH of 7 to 10 as shown in FIG. 1.

Figure 2:
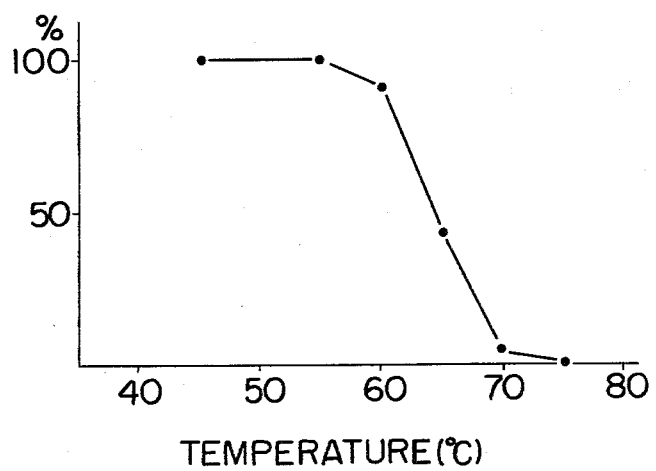
FIG. 2 is a graph of a curve indicating the thermal stability of L-lysine α-oxidase.

The thermal stability was also studied by incubation at pH 7.4 for 20 minutes at various temperatures. The enzyme was found to be stable at a temperature up to 55° C. as shown in FIG. 2.

(6) Optimum Temperature

The enzyme activity was determined at various temperatures in 0.1 M potassium phosphate buffer (pH 7.4). The optimum temperature of the present enzyme was observed to lie between 45° and 50° C.

(7) Inhibition, Activation and Stabilization

The enzyme activity was measured in the presence of various metallic ions and various additives. The enzyme was inhibited by copper ions, PCMB or mercuric chloride as shown in the following tables. The activator has not been found. The enzyme was stabilized by sodium chloride, potassium chloride, phosphates and the like.

| Metallic ions (1mM) | Relative activity(%) | Metallic ions (1mM) | Relative activity(%) |
|---|---|---|---|
| Zn | 92.7 | Ba | 100.0 |
| Co | 91.6 | Ca | 102.5 |
| Mn | 97.1 | Fe | 100.0 |
| Mg | 99.6 | Li | 98.4 |
| Cu | 78.5 | K | 100.0 |

| Inhibitors | Relative activity(%) |
|---|---|
| Cysteine | 100.3 |
| Glutathione | 103.5 |
| Tiron | 96.5 |
| N-Ethylmaleimide | 108.7 |
| EDTA | 93.8 |
| PCMB | 42.9 |
| Mercuric chloride | 19.2 |

Figure 3:
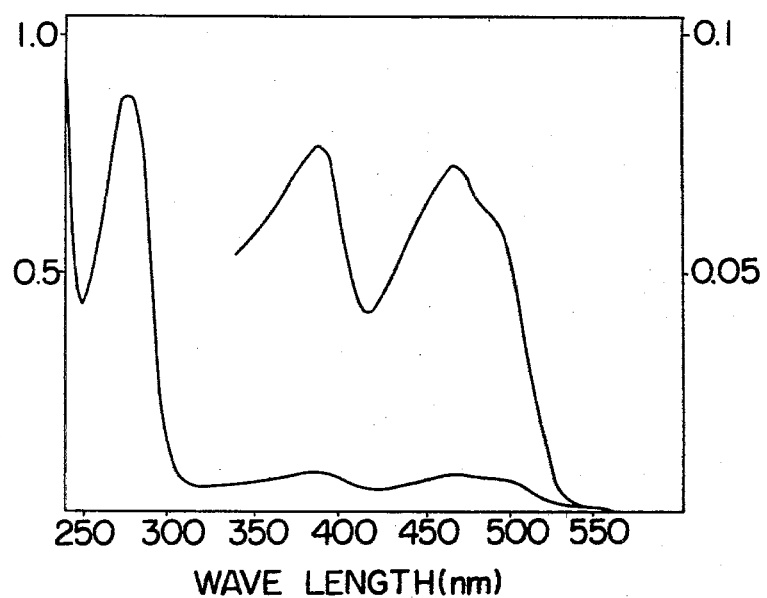
FIG. 3 is a graph indicating absorption spectrum.

(8) Absorption Spectrum (FIG. 3)

λmax: 277 nm (ε 247000), 388 nm (ε 24000), 466 nm (ε 22000).

$A_{1cm}^{1\%}$ at 280 nm: 21.7

A 280/A 260: 1.54.

(9) Coenzyme

The present enzyme preparation was subjected to thermal or TCA treatment and then to centrifugation. The absorption spectrum of the resulting supernatant was in agreement with that of flavin adenine dinucleotide (FAD). Furthermore, the supernatant activated the apoenzyme of D-amino acid oxidase. Thus, the coenzyme of the present enzyme was found to be FAD. The coenzyme was also identified as FAD from the Rf value of thin-layer chromatography. It was confirmed that two moles of FAD was present in each mole of the present enzyme.

(10) Polyacrylamide Gel Electrophoresis and SDS-polyacrylamide Gel Electrophoresis single band

(11) Isoelectric Point 4.35

(12) Sedimentation Constant $S^{\circ}_{20,w}$ 6.88

(13) Molecular Weight

The molecular weight of the present enzyme was found to be 112,000 (±10,000) by a gel filtration method using Sephadex G-200. The present enzyme contains two identical subunits, the molecular weight of the subunit being 56,000 (±5,000) according to an electrophoresis method using SDS-polyacrylamide gel. The molecular weight of the enzyme was also determined to be 119,000 by an ultracentrifuge sedimentation equilibrium method.

(14) Analysis of Amino Acids

The following data were obtained from calculation on the basis that the subunit has a molecular weight of 56,000.

| Amino acids | Numbers of amino acid residues (mol amino acid/mol subunit) | | | Estimated numbers of amino acid residues |
|---|---|---|---|---|
| | 24 hrs. | 48 hrs. | 72 hrs. | |
| Lysine | 26.1 | 26.1 | 26.8 | 26 |
| Histidine | 11.8 | 11.4 | 11.6 | 12 |
| Arginine | 15.9 | 14.8 | 15.3 | 15 |
| Aspartic acid | 57.6 | 61.2 | 59.2 | 59 |
| Threonine | 27.1 | 28.3 | 27.2 | 28 |
| Serine | 25.1 | 25.3 | 23.5 | 25 |
| Glutamic acid | 42.2 | 45.5 | 44.5 | 44 |
| Proline | 22.5 | 21.6 | 25.5 | 23 |
| Glycine | 39.5 | 42.9 | 42.5 | 42 |
| Alanine | 35.6 | 38.2 | 37.1 | 37 |
| ½ Cystine | | | | 7 |
| Valine | 24.5 | 27.6 | 26.9 | 26 |
| Methionine | 11.8 | 10.6 | 10.4 | 11 |
| Isoleucine | 19.6 | 22.0 | 22.7 | 21 |
| Leucine | 42.6 | 45.6 | 45.5 | 45 |
| Thyrosine | 30.5 | 27.8 | 27.1 | 28 |
| Phenylalanine | 19.5 | 20.5 | 21.1 | 20 |
| Tryptophan | | | | 16 |

II Production of L-lysine α-oxidase

L-lysine α-oxidase can be produced by culturing a strain belonging to the genus Trichoderma and having the ability to form L-lysine α-oxidase in a medium and isolating it from the culture. The process for production of the present enzyme will now be described in detail.

A. Microorganisms to be Used

The microorganisms to be used in the production of the present enzyme belong to the genus Trichoderma and have the ability to form L-lysine α-oxidase. Any strain having this fundamental properties can be used in the present invention, which includes newly-isolated strains found in nature, known cultured strains, and mutant strains having high ability to produce L-lysine α-oxidase which have been obtained by conventional artificial mutation methods, for example, physical treatments such as irradiation with ultraviolet rays, X-rays or γ-rays, and chemical treatments with nitrosoguanidine and the like. The process of the present invention utilizes basically the ability to synthesize L-lysine α-oxidase protein under the direction of the genes of Trichoderma microorganisms. Thus, in the present invention, the gene-recombined microorganisms can also be utilized. In such microorganisms, the genes of Trichoderma microorganisms concerned with the production of L-lysine α-oxidase have been combined with the bodies of other suitable microorganisms, for example, by the cell-fusion method using protoplast.

The novel strain, Trichoderma viride Y-244-2-90 which was isolated from the soil collected at Mt. Mitsumine, Saitama, Japan by the present inventors has an especially high ability to produce L-lysine α-oxidase. Accordingly, in the practice of the present invention, strains of Trichoderma viride such as Trichoderma viride Y244-2-90 and its mutants can be used suitably.

The above-mentioned strain was deposited on Oct. 7, 1977 with FERMENTATION RESEARCH INSTITUTE, AGENCY OF INDUSTRIAL SCIENCE and TECHNOLOGY, Inage, Chiba City, Japan under FERM-P No. 4256. The strain was also deposited on Dec. 29, 1978 with the AMERICAN TYPE CULTURE COLLECTION (ATCC), 12301 Parklawn Drive, Rockville, Md., U.S.A. under ATCC No. 20536. Further, the strain of FERM-P No. 4256 was sent directly from the FERMENTATION RESEARCH INSTITUTE, AGENCY OF INDUSTRIAL SCIENCE AND TECHNOLOGY to the AMERICAN TYPE CULTURE COLLECTION for deposition, and deposited with ATCC on Jan. 30, 1979 under ATCC No. 20538.

The taxonomical properties of the above-mentioned strain are given below.

(1) Growth on Culture Mediums

The above-mentioned strain was inoculated on the agar mediums given below and allowed to from giant colonies. The results of observation with the naked eye are shown in the following table.

| Mediums | State of colonies | Colors of reverse | Formation of conidia |
|---|---|---|---|
| Malt extract glucose agar medium | Hyphae are white and long, and grow thinly on the agar medium. Good growth | Colorless | Deep green conidia form on the peripheral region. |
| Czapek's agar medium | Hyphae are white and long, and grow very thinly on the agar medium. Inferior growth. | Colorless | Deep green conidia form thinly on the peripheral region. |
| Synthetic Mucor agar medium | Hyphae are white, long and felt-like. Good growth | Colorless | Deep green conidia form on the whole surface except the central region. |
| YpSs agar medium | Hyphae are white, long and felt-like. Good growth | Brownish | Deep green conidia form very thickly except the central region. |

(2) Morphological Features

The morphological features of the present strain which was cultured on a malt extract agar medium are shown in the following table, in comparison with those of Trichoderma viride IFO 4847 used as the control microorganism.

| Strains Organs | Trichoderma viride Y244-2-90 | Trichoderma viride IFO 4847 |
|---|---|---|
| Conidia lumps | 6 to 8μ | 7μ |
| Conidia | 2 to 3μ (sphere) | 3 to 4 × 3 to 8μ (spheroid) |
| Sterigmata | 2 to 3 × 8 to 10μ | 2 to 3 × 6 to 10μ |
| Branches of sterigmata | 2 to 3 | 2 to 3 |
| Conidiophores | 2 to 3μ | 2.5 to 3μ |
| Diameter of Hyphae | 3 to 4μ | 3 to 4μ |

By microscopic observation, the present strain was found to have unicellular green conidia formed massively at the tops of short verticillately-branched sterigmata. The types of the organs of the present strain are similar to those of Trichoderma viride IFO 4847. So far as the present inventors are aware, the IFO 4847 is one of the strains most closely resembling the present strain; however, they differ in the shapes of the conidia, the degrees of insertions of conidia, and some other features.

(3) Physiological Properties

(a) Assimilation of Carbon Source

The present strain was cultured with shaking at 28° C. for 6 days in the Czapeck's medium into which 2 to 3% of the following compound had been added as a sole assimilable carbon source. The state of growth is shown in the following table.

| Type of the carbon source | Degree of growth |
|---|---|
| glucose, maltose, arabinose, D-xylose, mannose, fructose, galactose, lactose, rhamnose, soluble starch | good growth |
| sucrose, raffinose, inulin | poor growth |

(b) Assimilation of Nitrogen Source

The present strain was cultured with shaking at 28° C. for 7 days in the Czapeck's medium into which 1% of the following compound had been added as a sole assimilable nitrogen source. The state of growth is shown in the following table.

| Type of nitrogen source | Degree of growth |
|---|---|
| sodium nitrate | good growth |
| gelatin, peptone, ammonium nitrate, ammonium sulphate, potassium nitrate, ammonium chloride | poor growth |

(c) pH for Growth

The present strain was cultured with shaking at 28° C. for 6 days in the YpSs medium whose pH had been adjusted as follows. The state of growth is shown in the following table.

| pH | 2 | 4 | 6 | 8 | 10 |
|---|---|---|---|---|---|
| State of growth | fair | good | good | good | poor |

(d) Temperature for Growth

When the present strain was cultured in the YpSs medium with shaking, its growth was good at 20° to 28° C. and poor at 37° C.

The present strain was classified from the above-mentioned mycological properties and especially from its morphological properties. The strain was identified to belong to class of Fungi Imperfecti, sub-class of Deutromycetes, order of Moniliales, family of Moniliaceae, genus of Trichoderma and to be one of strains of *Trichoderma viride*, in accordance with "Ainswarth and Bisby's Dictionary of Fungi, 5th ed. (1961)" by G. C. Ainswarth.

B. Methods and Conditions for Culture

The methods and conditions of culturing microorganisms to produce L-lysine α-oxidase are not especially restricted provided they are not counter to the achievement of the objects of the present invention. In other words, methods and conditions which provide the environment capable of culturing productive microorganisms and producing L-lysine α-oxidase can be used.

From the present inventors' researches on the wild strain *Trichoderma viride* Y244-2-90, it has been found that the production of L-lysine α-oxidase with the present strain can be carried out more advantageously in solid mediums than in liquid mediums. The strain suitable for liquid-medium culture methods, however, can be obtained by strain-improvement techniques. Therefore, the standard methods and conditions for culture in the production of L-lysine oxidase by using a wild strain Y244-2-90 are shown herein and, of course, these methods and conditions may be suitably modified according to the types and properties of the microorganisms to be used.

Examples of solid mediums which can be used in a solid-medium culture method include the so-called wheat bran mediums prepared by spraying 60 to 80% by weight of water onto a commercial wheat bran, and natural cereal mediums containing rice, rice bran, corn and the like; mediums prepared by adding to the above-mentioned medium suitable amounts of a carbon source (e.g., glucose, glycerol, maltose, soluble starch, ethanol, etc.), a nitrogen source (amino acids, peptone, soy bean powder, protein hydrolyzates, corn steep liquor, meat extract, yeast extract, sodium nitrate, etc.), and minor components (sodium salts, potassium salts, manganese salts, calcium salts, zinc salts, phosphates, sulphates, etc.), which can be assimilated by the present strain; and mediums prepared by mixing these mediums in suitable compositions and granulating the mixture into suitable sizes and shapes.

The conditions for culture are a temperature of 20° to 30° C., a pH range of 4 to 8, and a period of 3 to 25 days.

In liquid-medium culture methods, it is possible to employ a variety of selections and formulations of carbon sources, nitrogen sources and minor components which can be assimilated by the present strain. For example, it has been confirmed that L-lysine α-oxidase can be produced by aerobic cultures employing a malt extract medium (malt extract 2%, glucose 2%, peptone 0.1%), a Saburaud's medium (maltose 4%, peptone 1%), a YpSs medium (soluble starch 1.5%, yeast extract 0.4%, dipotassium phosphate 0.1%, magnesium sulphate heptahydrate 0.05%), or a sporulation medium (glucose 1.5%, Casamino acid 0.5%, malt extract 0.1%, yeast extract 0.1%, glycerol 1%). The culture is preferably carried out under a sufficient supply of oxygen in any medium. Thus, a shaking culture method and an aerated-agitation culture method are generally employed. The other conditions for culture are similar to those of solid medium culture methods.

It has been found that the present process for production of L-lysine α-oxidase be carried out most efficiently in the following manner. *Trichoderma viride* Y244-2-90 or its artificial mutant strain is employed as the microorganism to produce L-lysine α-oxidase. When the *Trichoderma viride* Y244-2-90 is employed, the strain is cultured in a wheat bran medium humidized with 70% by weight of water at 28° C. for 14 days, and the resulting culture product is subjected to extraction with water to obtain a crude extract of L-lysine α-oxidase. This mode of producing L-lysine α-oxidase will be further explained in detail in Example 1. Changes and modifications of the embodiments of the invention such as in scale size can be optionally made, and the present invention should not be restricted by these embodiments and examples thereof.

C. Preparation and Purification of L-lysine α-oxidase

L-lysine α-oxidase can be produced by culturing the microorganisms capable of producing the oxidase as described above. The forms of preparation as the enzyme preparations should be employed optionally in accordance with the uses of the enzyme preparations. The preparations may be in the form whose L-lysine α-oxidation activity can be utilized practically and in the form of fungous cells separated from the culture, treated fungous cells, culture liquids, culture filtrates, culture extracts, partly-purified enzyme solution or powder, purified enzyme powder or solution and the like.

In order to isolate L-lysine α-oxidase, the fungous cells may be collected from the culture, and L-lysine α-oxidase may be extracted with a suitable buffer solution, under an ultrasonic treatment or a mechanical milling.

The present enzyme, however, can be efficiently collected directly from the liquid culture or the water-extract of solid culture since the enzyme is readily secreted out of the fungous cells. The purified preparation of L-lysine α-oxidase which is electrophoretically pure can be obtained from the resulting crude enzyme solution by conventional methods such as, dialysis method, salting out with ammonium sulphate, etc., precipitation with organic solvents such as ethanol and acetone, ion-exchange chromatography such as DEAE-cellulose chromatography, and DEAE-Sephadex chromatography adsorption chromatography such as hydroxy apatite chromatography, and gell filtration method using Sephadex G-200 and the like.

II Utility of L-lysine α-oxidase-assay of lysine

As described above, the L-lysine α-oxidase can be utilized to determine L-lysine.

In the method of the present invention, the form and purity of the preparation can be suitably selected in accordance with the types of the detection system of the indicating substance which is connected with the decomposition reaction of L-lysine by the action of the present enzyme. In other words, the presence of contaminating substances in L-lysine α-oxidase enzyme preparations is permissible, provided that the contaminating substances do not interfere with the decomposition of L-lysine and the reactions and/or detection in the detection system of an indicating substance. The enzyme preparation can also be prepared in the form of a soluble enzyme or an adsorbed or immobilized enzyme on a suitable carrier.

The pH range for the enzymatic reaction of L-lysine α-oxidase when the enzyme of Trichoderma is used is from 5 to 10, preferably from 7 to 10. The temperature is not higher than 60° C. and preferably from 30° to 55° C. A variety of buffer solutions are preferably used as the enzymatic reaction medium in order to maintain the optimum pH. As the buffer solutions, any buffer solution which can maintain the pH range described above and will not inhibit the enzymatic reaction can be used, examples of which are a conventional phosphate buffer, Tris-hydrochloric acid buffer, acetate buffer, borate buffer, glycine-potassium hydroxide buffer and the like.

The method for specific determination of L-lysine in accordance with the present invention comprises a combination of the enzymatic reaction by the action of L-lysine α-oxidase, with the detection system of an indicating substance which detects and measures the quantity of oxygen consumed in the course of the present enzymatic reaction or the amount of hydrogen peroxide, ammonia, α-keto-ε-aminocaproic acid or $\Delta^1$-piperideine-2-carboxylic acid (an intramolecular dehydrated form of α-keto-ε-aminocaproic acid) which has been produced in the course of the reaction. The detection system of these indicating substances can be optionally selected, and the objects of the present invention can be achieved with any of these substances. The method for detection of the indicating substance is not especially restricted. Thus, it is possible to combine the various methods of detecting and measuring oxygen, hydrogen peroxide, ammonia, α-keto-ε-aminocaproic acid or $\Delta^1$-piperideine-2-carboxylic acid, with the L-lysine α-oxidase enzyme reaction. In the following description representative methods for detection and measurement of each indicating substance are set forth. The detection methods for these indicating substances, however, are not restricted to the conventional methods. The methods to be developed in the future can also be employed.

The methods of measuring the quantity of oxygen consumed include the Warburg's manometer method and the oxygen electrode method. A modification of the oxygen electrode method is illustrated by a method in which use is made of an enzyme-electrode which comprises an oxygen electrode such as the Clark's complex electrodes or the Galvanic electrodes on the top of which L-lysine α-oxidase is deposited. When the enzyme electrode is employed, the concentration of L-lysine can be determined by measuring an oxygen-consuming velocity with the electrodes placed in a sample solution containing L-lysine. It is also possible to determine the concentration of L-lysine by combining a nuclear electrode and a compensation electrode, and measuring the electric current and electric potential difference between the two electrodes. The deposition of L-lysine α-oxidase on the top of the oxygen electrode is effected by, for example, confining a soluble enzyme or an enzyme which has been fixed chemically or physically to a suitable carrier at the top of the electrodes by means of a semi-permeable membrane or the like, or covering the top of the electrode with a collagen membrane or a porous organic high-molecular membrane to which an enzyme has been fixed. A variety of methods of fixing the enzyme onto carriers can be employed, example being a method of putting the enzyme occluded in polyacrylamide gel, a method of mixing the enzyme and another inactive protein and crosslinking both the components with glutaric aldehyde, and a method of fixing the enzyme onto organic high-molecular powder.

The methods of detecting and measuring hydrogen peroxide are classified into three methods, namely, spectroscopic methods, electrochemical methods and fluorescence methods.

The spectroscopic method of measuring hydrogen peroxide is represented by the combination of an activating agent of hydrogen peroxide and an indicator. Examples of effective activating agent of hydrogen peroxide, are, for example (1) the peroxidases of horse-radish, sweet potatoes, and the like, (2) an iodide, a molybdate and the like and (3) mixtures thereof. Examples of the indicator are o-dianisidine; o-tolidine; o-toluidine; 2,6-dichloroindophenol; benzidine; 3,3'-5,5'-tetraalkylbenzidines (3,3'-dimethyl-5,5-diethylbenzidine; 3,3'-5,5'-tetramethylbenzidine; 3,3'-5,5'-tetraethylbenzidine; 3,3'-5,5'-tetraisopropylbenzidine, etc.), 4-methoxy-1-naphthol, 2,2'-azino-di-[3-ethylbenzthiazoline sulfonic acid-(6)]-diammonium salt; and combined indicators. The combined indicator is represented by the combination of 4-aminoantipyrine and phenol, but is not restricted to this combination. For example, instead of phenol, polyhydric alcohols or phenol derivatives such as 2,4-dichlorophenol, catechol, resorcinol, hydroquinone, cresol, guaiacol, pyrogallol and orcinol, or aniline or aniline derivatives such as dimethyl aniline and diethyl aniline can be used. On the other hand, instead of 4-aminoantipyrine, 4-aminophenazone, 4-aminopyrazolone derivatives as well as 3-methylbenzothiazolone-hydrazone (MBTH) and its sulfonic acid derivatives, and the like can be used. In addition to the above-described indicators, any indicator can be employed provided that it is quantitatively oxidized under the condition of determination to exhibit change in color.

Other spectroscopic methods of measuring hydrogen peroxide include a method which comprises forming formaldehyde from hydrogen peroxide in the presence of methanol and catalase and reacting the resulting formaldehyde with a hydrazone [e.g., 3-methyl-2-(sulphonyl)-benzothiazolone hydrazone, 3-methylbenzothiazolone hydrazone, and 4-amino-3-hydrazino-5-mercapto-1,2,4-triazol,] in the presence of an oxidizing agent (e.g., potassium cyanoferrate, ferric chloride, cerium (IV) ammonium sulphate, and orotic acid).

The methods of determining hydrogen peroxide by measuring the change by absorption spectrum of NADH or NADPH include a method of converting glutathione into an oxidized glutathione in the presence of hydrogen peroxide-glutathione peroxidase, reducing it with glutathione reductase in the presence of NADPH, and then measuring the oxidized amount of NADPH (Analytical Biochemistry, Vol. 76, p.p. 184–197, 1976) and a method of oxidizing NADH with hydrogen peroxide-NADH peroxidase and measuring the change in the optical density (Japanese Laid-Open Patent Publication No. 15492/1978). Moreover, also known are the catalase-acetylacetone method, the method of oxidizing alcohol with aldehyde dehydrogenase, the method of oxidizing and decolorizing indigo carmine with a copper ion-histamine system and measuring the degree of its decolorization, and the others.

The electrochemical methods for determination of hydrogen peroxide include a polarographic method using platinum electrodes, a method which comprises using a catalase-enzyme electrode and measuring the degree and the velocity of the increase of oxygen level, and a method of oxidizing iodine anions to iodine with hydrogen peroxide in the presence of a molybdate catalyst and determining the iodine-forming velocity by means of a potentiometer or an ammeter.

A known fluorescence method for determination of hydrogen peroxide comprises converting homovanillic acid into a fluorescent 2,2'-dihydroxy-3,3'-dimethoxydiphenyl-5,5'-diacetyl acid with hydrogen peroxide and peroxidase and measuring the initial velocity of formation of the fluorescent product. Other substances than homovanillic acid which can be converted into fluorescent products with hydrogen peroxide and peroxidase are, for example, p-hydroxyphenyl acetic acid, diacetyl-2', 7'-dichlorofluorescein and the like. Also is known a method which comprises oxidizing a fluorescent substance such as 6-methoxy-7-hydroxy-1,2-benzopyrone, 3,5-diacetyl-1,4-dihydrolutidine into the corresponding non-fluorescent substance with hydrogen peroxide-peroxidase, and measuring the decrease in fluorescence in the reaction system.

The methods for determination of ammonia include the conventional Nessler's method, phenosafaanin method ninhydrin method, indophenol method, ammonia ion electrode method, and a method of measuring the change in optical density caused by the reaction of glutamic acid dehydrogenase with α-ketoglutarate in the presence of NADH or NADPH. Satisfactory results can be obtained by employing any of these methods.

The methods for determination of α-keto-ε-aminocaproic acid include the color-developing method using 3-methyl-2-benzothiazolone hydrazone, the 2,4-dinitrophenyl hydrazine method and the like. As a method for specific determination of Δ1-piperideine-2-carboxylic acid which is an intramolecular dehydrated form of α-keto-ε-aminocaproic acid, a colorimetric method using o-aminobenzaldehyde is known. These methods can be satisfactorily applied in the present invention.

The methods for determination of L-lysine in accordance with the present invention are based upon the above-described principles and procedures. The operations of the determination, however, are not especially restricted to the embodiments described herein and can be optionally carried out. For example, the operation of determination can be simplified by fixing L-lysine α-oxidase in a test tube. A rapid-test paper or film can be provided by impregnating testing paper or film with the L-lysine α-oxidase as well as a peroxidase and an indicator.

The present invention will be further described by way of the following non-limitative examples thereof.

EXAMPLE 1 (Production of Enzyme)

In a 300 ml conical flask were charged 8 g of wheat bran, 5 ml of water and 1 g of rice hulls. The mixture was subjected to sterilization at 120° C. for 30 minutes to prepare a wheat-bran medium for seeding. The Trichoderma viride Y244 -2-90 (FERM-P No.4256 and ATCC No. 20536) was inoculated onto the wheat-bran medium and cultured at 28° C. for 7 days to prepare seed molds.

Into each of six 5-liter conical flasks were placed 200 g of wheat bran and 140 ml of water. This step was followed by sterilization at 120° C. for 30 minutes to prepare a culture medium. The above-mentioned seed mold was inoculated under germ-free conditions on the media and cultured at 28° C. for 14 days. The resulting culture was immersed in 9 liters of water for 1 hour, filtered and then passed through "Super cell" (supplied by Johns-Manville) to obtain about 9 liters of crude enzyme solution. Ammonium sulfate was added to this crude enzyme solution in a quantity to reach 30% of the saturated concentration, whereupon insolubles were separated, and the insolubles were removed by centrifugation. Ammonium salfate was further added to the supernatant to reach 60% of the saturated concentration to produce a precipitate. The separated precipitate was then dissolved in 500 ml of 0.02 M potassium phosphate buffer (pH 7.4), and the resulting solution was subjected to dialysis overnight with the same buffer solution. The precipitate formed in the course of the dialysis treatment was removed by centrifugation, and the resulting supernatant was applied on a DEAE-cellulose column (3.5×27 cm) which had been equilibrated with the same buffer solution. The column was washed with the same buffer solution containing 0.15 M sodium chloride, and then the adsorbed enzyme was eluted with the same buffer solution containing 0.2 M sodium chloride. The eluted active fractions were collected, dialyzed and concentrated, and then subjected to gel filtration with "Sephadex G-200" column (2×140 cm). Active fractions were collected and ammonium sulfate was added thereto in an amount of 60% of the saturated concentration. The separated precipitate was collected by centrifugation and dissolved in 5 ml of 0.02 M Tris-hydrochloric buffer (pH 8.4) containing 0.1 M of sodium chloride. This step was followed by dialysis overnight with the same buffer solution.

The dialyzed internal solution was subjected to centrifugation. The resulting supernatant was applied on a DEAE-Sephadex A-50 column (0.7×4 cm), and the column was washed with 0.02 M Tris-hydrochloric acid buffer containing 0.15 M of sodium chloride. The adsorbed enzyme was then eluted with the same buffer solution containing 0.2 M of sodium chloride. Active fractions were collected and subjected to dialysis with 0.01 M potassium phosphate buffer. The dialyzed internal solution was subjected to centrifugation and the resulting supernatant was freeze-dried to obtain 18.4 mg of a purified preparation of L-lysine α-oxidase (yield 6.6%, specific activity 85.5 units/mg of protein).

EXAMPLE 2 (Determination of L-lysine)

Color-developing reagent: 45 mg of phenol, 25 mg of 4-aminoantipyrine, and 8 mg of horseradish peroxidase (100 units/mg) were dissolved in 50 ml of 0.25 mol potassium phosphate buffer (pH 7.4).

L-lysine α-oxidase: 70 μg of the purified enzyme (85.5 units/mg) was dissolved in 30 ml of 0.02 mol potassium phosphate buffer (pH 7.4) (0.2 unit/ml). The L-lysine α-oxidase used was produced from *Trichoderma viride* Y244-2-90 (FERM-P No. 4256 and ATTC No. 20536) in accordance with the process of the above-described Example 1.

Figure 4:
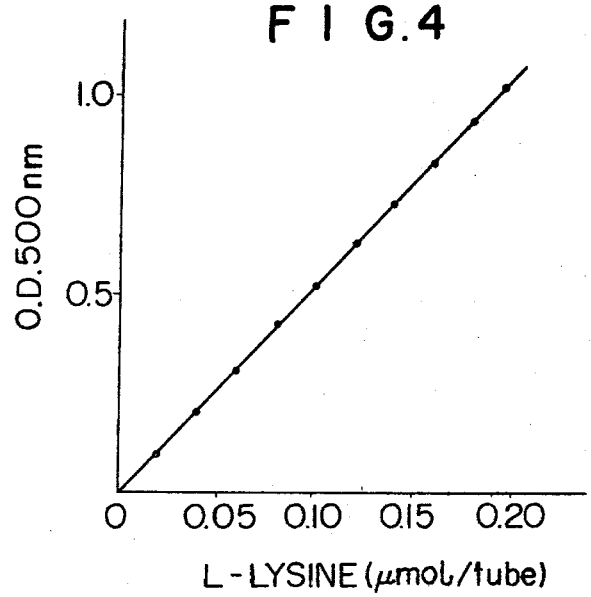
FIGS. 4 through 6 are graphs of calibration curves which were drawn in examples of determination of L-lysine in accordance with the present invention.

Operations: 0.7 ml of a color-developing reagent was taken in a test tube and 0.1 ml of L-lysine α-oxidase was added thereto. After thorough mixing, the tube was subjected to incubation conditions at 37° C. for 5 minutes. 0.2 ml of a standard L-lysine solution (0 to 1μ mol/ml) or a sample solution was added, and the mixture was allowed to start reacting. The mixture was incubated under an aerobic condition with shaking for 20 minutes. This step was followed by measurement of the optical density at 500 nm using a control mixture containing no L-lysine α-oxidase. A calibration curve was drawn therefrom, and the L-lysine content in the sample was determined. The calibration curve is shown in FIG. 4.

The reliability of the method of the present invention was tested by estimating the known quantity of L-lysine which had been added to the aminoacid calibration mixture containing equimolar quantities of 17 kinds of amino acids and ammonia. The quantitative recovery of L-lysine was observed as shown in Table 1. A variety of serums to which 0 to 0.3μ mol/ml of L-lysine had been added were also used as the samples without further treatment. The results are shown in the following Table 2.

TABLE 1

| Quanity of L-lysine added to the standard amino acid mixture (μmol) | Determination data of L-lysine in accordance with the present invention (μmol) |
| --- | --- |
| 0 | 0.054 |
| 0.025 | 0.080 |
| 0.050 | 0.104 |
| 0.100 | 0.153 |
| 0.140 | 0.194 |

TABLE 2

| Quantity of L-lysine added to serum (μmol/ml serum) | Determination data of L-lysine in accordance with the present invention (μmol/ml serum) | | | |
| --- | --- | --- | --- | --- |
| | human being | horse | bovine | calf |
| 0 | 0.12 | 0.08 | 0.09 | 0.14 |
| 0.2 | 0.36 | 0.30 | 0.32 | 0.36 |
| 0.4 | 0.56 | 0.54 | 0.52 | 0.58 |
| 0.8 | 1.00 | 0.94 | 0.96 | 1.00 |
| 1.6 | 1.72 | 1.68 | 1.76 | 1.84 |
| 3.2 | 3.28 | 3.26 | 3.40 | 3.44 |

EXAMPLE 3 (Determination of L-lysine)

Figure 5:
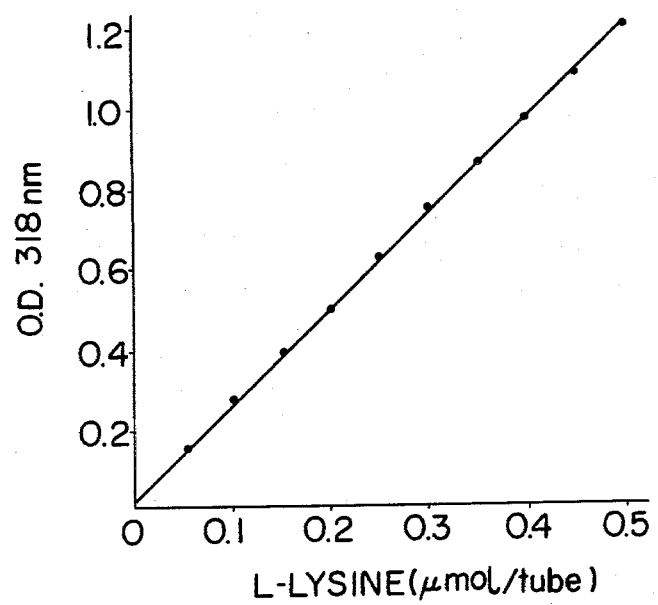

In a test tube were placed 0.7 ml of a 0.1 M potassium phosphate buffer (pH 8.0), 0.1 ml of catalase (3250 units/ml) and 0.1 ml of L-lysine α-oxidase (0.4 unit/ml) prepared in accordance with the process of Example 1. The mixture was preheated at 37° C. for 5 minutes. Reaction was started by the addition of 0.1 ml of a standard L-lysine solution (0 to 5μ mol/ml) or a sample solution. The reaction mixture was incubated under an aerobic condition with shaking at 37° C. for 20 minutes, and the reaction was terminated by the addition of 0.1 ml of 25% trichloroacetic acid. To the reaction-terminated solution were added 1.9 ml of a 1 M acetate buffer (pH 5.0) and 0.8 ml of a 0.1% 3-methyl-2-benzothiazolone hydrozone (hydrochloride) solution. The mixture was agitated and then incubated at 50° C. for 30 minutes. This step was followed by cooling of the mixture to room temperature. The optical density at 318 nm was measured against a control mixture containing no L-lysine α-oxidase to obtain a calibration curve. The calibration curve is shown in FIG. 5.

EXAMPLE 4 (Determination of L-lysine)

Figure 6:
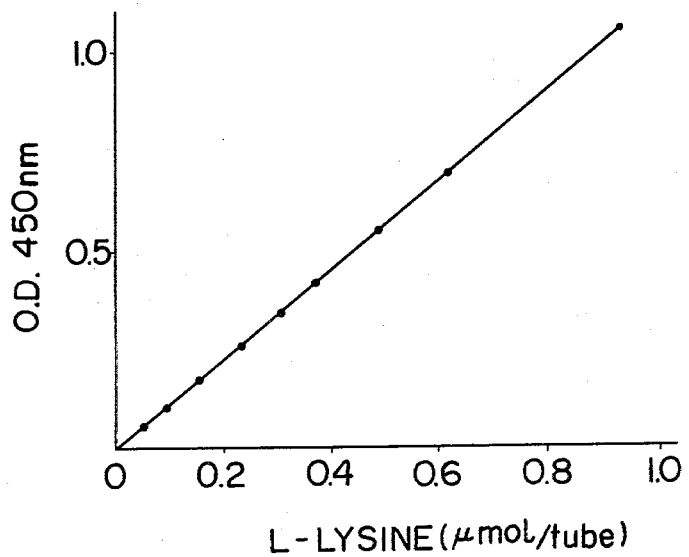

To the enzyme reaction-terminated solution of L-lysine α-oxidase which had been prepared as in Example 3, was added 5 ml of a 0.02 M o-aminobenzaldehyde solution dissolved in 0.2 M potassium phosphate buffer (pH 8.0). This step was followed by incubation at 37° C. for 1 hour. The optical density at 450 nm was measured to prepare a calibration curve. The calibration curve is shown in FIG. 6.

The abbreviations used herein are as follows.
Km: Michaelis constant
NADH: Nicotinamide adenine dinucleotide reduced form
NADP: Nicotinamide adenine dinucleotide phosphate
NADPH: Nicotinamide adenine dinucleotide phosphate reduced form
PCMB: para-Chloromercuribenzoic acid
EDTA: Ethylendiaminetetraacetic acid
DEAE: Diethylaminoethyl
SDS: Sodium dodecyl sulfate
TCA: Trichloroacetic acid
IFO: Institute for Fermentation, Osaka (Japan)

What is claimed is:

1. A method for determination of L-lysine in a sample, which comprises subjecting L-lysine contained in the sample to decomposition by the use of L-lysine α-oxidase in the presence of oxygen, and determining the quantity of oxygen consumed in the course of the decomposition or the quantity of hydrogen peroxide, ammonia, α-keto-ε-aminocaproic acid or Δ$^1$-piperideine-2-carboxylic acid produced in the course of the decomposition.

2. The method for determination of L-lysine as set forth in claim 1, in which the L-lysine α-oxidase is an enzyme which is a product of aerobic culture of a strain belonging to the genus Trichoderma.

3. The method for determination of L-lysine as set forth in claim 1, in which the L-lysine α-oxidase is an L-amino acid oxidase having an ability to form α-keto-ε-aminocaproic acid, ammonia and hydrogen peroxide from L-lysine by oxidative deamination of L-lysine in the presence of water and oxygen as well as having a very low Km value with respect to L-lysine and the high substrate-specificity with respect to L-lysine.

4. The method for determination of L-lysine as set forth in claim 3, in which the coenzyme thereof is flavin adenine dinucleotide.

5. The method for determination of L-lysine as set forth in claim 3 or 4, in which the enzyme has a molecular weight represented by two subunits each having a molecular weight of 56,000 (±5,000) determined according to an electrophoresis method using SDS-polyacrylamide gel, a molecular weight of 112,000 (±10,000) determined according to a gel filtration method, and a molecular weight of about 119,000 determined according to ultracentrifuge sedimentation equilibrium method.

* * * * *